United States Patent
Aufrichtig et al.

(10) Patent No.: US 7,272,207 B1
(45) Date of Patent: Sep. 18, 2007

(54) PROCESSES AND APPARATUS FOR VARIABLE BINNING OF DATA IN NON-DESTRUCTIVE IMAGING

(76) Inventors: Richard Aufrichtig, 2175 Mission College Blvd., Santa Clara, CA (US) 95054; John Robert Lamberty, 3000 N. Grandview Blvd., Waukesha, WI (US) 53188; Paul Richard Granfors, 2175 Mission College Blvd., Santa Clara, CA (US) 95054

(*) Notice: Subject to any disclaimer, the term of this patent is extended or adjusted under 35 U.S.C. 154(b) by 0 days.

(21) Appl. No.: 11/389,271

(22) Filed: Mar. 24, 2006

(51) Int. Cl.
   *H05G 1/58* (2006.01)

(52) U.S. Cl. ............... 378/116; 378/19; 378/98.8; 378/210

(58) Field of Classification Search ............ 378/19, 378/62, 98.8, 116, 117, 207, 210

See application file for complete search history.

(56) References Cited

U.S. PATENT DOCUMENTS 5,848,123 A * 12/1998 Strommer ............... 378/98.8
6,663,281 B2    12/2003 Aufrichtig et al.
2007/0076842 A1* 4/2007 Tkaczyk et al. ........... 378/5

OTHER PUBLICATIONS

Granfors, P., "Performance Of A 41×41 cm2 Amorphous Silicon Flat Panel X-ray Detector Designed For Angiographic And R&F Imaging Applications", Med. Phys. 30(10), Oct. 2003, pp. 2715-2726.

* cited by examiner

*Primary Examiner*—Jurie Yun
(74) *Attorney, Agent, or Firm*—Peter Vogel; Ellis B. Ramirez (57) ABSTRACT

Systems, processes and apparatus are described through which non-destructive imaging is achieved, including a process for variable binning of detector elements. The process includes accepting input data indicative of image quality goals and descriptors of an imaging task, as well as parameters characterizing a test subject, relative to non-destructive imaging of an internal portion of the test subject and determining when the non-destructive imaging system is capable of achieving the image quality goals using binning of more than four pixels.

20 Claims, 7 Drawing Sheets

PROCESSES AND APPARATUS FOR VARIABLE BINNING OF DATA IN NON-DESTRUCTIVE IMAGING

FIELD OF THE DISCLOSURE

This disclosure relates generally to nondestructive evaluation, including medical diagnosis, and more particularly to techniques for facilitating diagnosis of presenting conditions based on internal images of a test subject, such as a living patient.

BACKGROUND

Many medical diagnoses rely on non-invasive diagnostic tools to provide information, often in the form of images, descriptive of status of internal portions or organs of a patient. These tools include thermal imaging, ultrasonic probes, magnetic resonance imaging techniques, positron emission tomography, computed tomography (CT), single photon emission-computed tomography (SPECT), optical imaging and/or X-ray based techniques. In some minimally invasive instances, imaging aids, such as contrast-enhancing agents, are introduced into the subject or patient to aid in increasing available data content from the non-destructive imaging technique or techniques being employed.

Each of these tools presents advantages in particularized situations, has technological limitations, may require set-up and analysis time, can include risks and also has associated costs. As a result, a cost-benefit analysis that also reflects the degree of urgency with respect to a particular diagnostic trajectory often favors usage of X-ray based measurement techniques.

However, exposure to X-rays can result in some risk to the test subject or patient. For at least this reason, the dosage of X-rays incident on the patient, organ or object being evaluated/imaged, is often carefully chosen and controlled, for example, variables such as current to the X-ray tube, peak voltage applied to the X-ray tube (kVp) and exposure time, and by selecting and defining an area to be exposed to provide successful imaging, based on the task and the test subject or patient's parameters, with least health risk to the patient or radiation exposure to the object being imaged. The Food and Drug Administration has recently identified X-rays as potentially having carcinogenic effects, adding impetus to the desire to reduce overall exposure while still providing imaging characteristics capable of enabling rapid, effective and accurate diagnostic aids.

Several factors influence image quality resulting from an X-ray procedure. Statistical photon noise resulting from characteristics of the X-ray source and the X-ray generation conditions tends to dominate other noise sources in formation of an X-ray image. Contrast between various image portions, and contrast enhancement techniques, are also important considerations in providing diagnostic images, and these issues require increasingly sophisticated treatment as dose is decreased.

One of the key tenets of medical X-ray imaging is that image quality should be carefully considered in determining exposure conditions, such as predetermined dose considerations delivered to the test subject or patient. The design and operation of a detector used for medical X-ray imaging should therefore be tailored, responsive to the particularized task and measurement conditions, including variables in test subject mass, opacity and the like, to provide high image quality for each X-ray exposure that is incident at its input. One very useful objective metric of quality for electronically-represented images, per input exposure, is detective quantum efficiency (DQE), which represents efficiency of transfer of signal-to-noise ratio from the input signal (i.e., the exposure employed) to detector output.

Pixelated X-ray detectors (detectors comprising a geometric array of multiple detector elements, where each detector element may be individually representative of at least a portion of a picture element in the resultant image) are increasingly being used, particularly for medical imaging. The resulting electrical signals from pixelated detectors may be "read out" individually. Examples of such usage include full resolution (one by one binning), full field of view imaging, in which each detector element in an array individually represents a pixel, and region of interest imaging, in which a subset of the total ensemble of detector elements may each correspond to a pixel, but not all detector elements are employed.

Detector arrays may also be employed in modes in which the signals from more than one individual detector element are combined, prior to electrical conditioning of the resulting electrical signals. Such combination is commonly called "binning" of individual detector signals. In turn, digital or electronic detectors of X-rays and subsequent signal processing of the signals from such detectors increase flexibility in application and thus help to promote reduction of dose of the illumination being employed for non-destructive imaging, which is a desirable goal. The problems addressed by this disclosure involve successfully employing these capabilities to improve performance of a detector array for a particular imaging task.

For the reasons stated above, and for other reasons discussed below, which will become apparent to those skilled in the art upon reading and understanding the present disclosure, there are needs in the art to provide test data in support of reliable diagnoses of medical conditions and diseases from medical anatomical images, providing contrast equal to or exceeding that of conventional approaches, yet using reduced exposure parameters when feasible, consistent with the imaging task.

SUMMARY

The above-mentioned shortcomings, disadvantages and problems are addressed herein, which will be understood by reading and studying the following disclosure.

In one aspect, a process for variable binning of detector pixels in a non-destructive imaging system is disclosed. The process includes accepting input data indicative of image quality goals and descriptors of an imaging task, as well as parameters characterizing a test subject, relative to non-destructive imaging of an internal portion of the test subject and determining when the non-destructive imaging system is capable of achieving the image quality goals using binning of more than four pixels.

In another aspect, a non-destructive imaging system includes an illumination source configured to internally illuminate a test subject and a detector array including a mosaic of detector elements aligned with the illumination source opposite the test subject. Each detector element corresponds to a pixel in a full resolution, full field of view, imaging mode of the detector array. The system also includes a controllable driver coupled to the detector array. The controllable driver provides capability for multiple detector array functionality settings including binning of more than four pixels. The system also includes an interface capable of accepting input data indicative of image quality goals and facilitating selection of at least one of the multiple functionality settings.

In a yet another aspect, an article of manufacture embodies computer code thereon that includes computer-readable instructions, which, when executed by one or more processors, causes the one or more processors to perform acts of (i) accepting input data indicative of image quality goals and information descriptive of a test subject to be characterized using an X-ray system and (ii) determining when the X-ray system is capable of achieving the image quality goals via pooling of analog data derived from an extended group of pixels.

Systems, clients, servers, processes, and computer-readable media of varying scope are described herein. In addition to the aspects and advantages described in this summary, further aspects and advantages will become apparent by reference to the drawings and by reading the detailed description that follows.

DETAILED DESCRIPTION

In the following detailed description, reference is made to the accompanying drawings that form a part hereof, and in which are shown, by way of illustration, specific embodiments which may be practiced. These embodiments are described in sufficient detail to enable those skilled in the art to practice the embodiments, and it is to be understood that other embodiments may be utilized, and that logical, mechanical, electrical and other changes may be made without departing from the scope of the embodiments.

As used herein, the term "illumination" refers to exposure to photons, electromagnetic radiation, phonons (e.g., insonification via ultrasound) or other wave phenomena, which do not necessarily correspond to light that is visible to a human eye. As employed herein, "an extended group of pixels" is defined to describe five or more pixels whose output signals are pooled or combined, for example, are added, to form a single picture element or pixel, prior to or after conversion to binary data, but prior to post-exposure processing and/or storage or display of resultant diagnostic data including images derived from a source of such pixels. Ranges of parameter values described herein are understood to include all subranges falling therewithin. The following detailed description is, therefore, not to be taken in a limiting sense.

The detailed description is divided into five sections. In the first section, a system level overview is described. In the second section, modeling schemes for selecting among pixel binning options in at least portions of one or more images are described. In the third section, embodiments of processes are described. In the fourth section, hardware and an operating environment in conjunction with which embodiments may be practiced are described. In the fifth section, a conclusion of the detailed description is provided. A technical effect of the systems and processes disclosed herein includes at least one of facilitating capability for selective, real-time, adaptive variable binning of data from a plurality of detector elements coupled together in a sensing array to provide image quality adapted to the imaging task together with reduced dose delivered to the test subject in non-destructive imaging.

I. SYSTEM OVERVIEW

Figure 1:
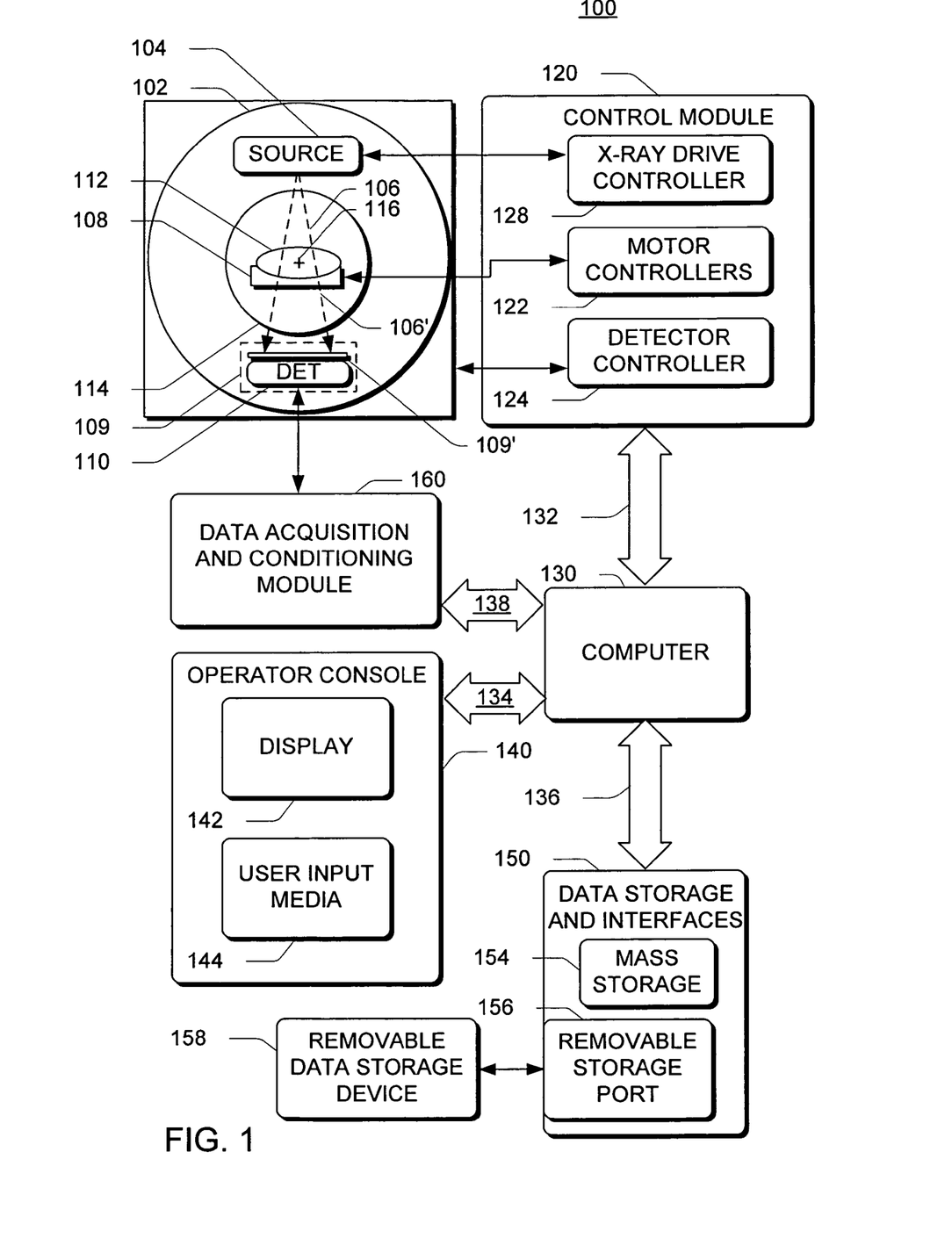
FIG. 1 is a simplified block diagram of an overview of a system configured to improve X-ray imaging operations.

FIG. 1 is a simplified diagram of an overview of a system 100 configured to improve X-ray imaging operations. In particular, the system 100 is configured to provide digitized images from non-destructive imaging systems based on X-radiation, while reducing the radiation dose delivered to the object or patient being imaged, compared to conventional X-ray imaging systems and processes. The system 100 includes a gantry 102 or other support for an illumination source 104, such as an X-ray illumination source, capable of providing illumination 106, such as X-rays or other non-destructive internal imaging illumination, a test subject support 108 that is transmissive with respect to the illumination 106 and that is positioned above a detector assembly 109, which may include a scintillator 109', and which includes an image capture device 110, opposed to the illumination source 104.

Components of the system 100 and a test subject 112 are maintained in a defined geometric relationship to one another by the gantry 102. A distance between the illumination source 104 and the detector 110 may be varied, depending on the type of examination sought, and the angle of the illumination 106 respective to the test subject 112 can be adjusted with respect to the body to be imaged responsive to the nature of imaging desired.

The test subject support 108 is configured to support and/or cause controlled motion of the test subject 112, such as a living human or animal patient, or other test subject 112 suitable for non-destructive imaging, above the detector 110 so that illumination 106' is incident thereon after passing through the test subject 112. In turn, information from the detector 110 describes internal aspects of the test subject 112.

The detector assembly 109 may include a scintillator 109', such as a conventional CsI scintillator 109', optically coupled to an array of photodiodes (FIGS. 2 and 3, infra), such as a two-dimensional array of photodiodes and suitable control transistors formed using semiconductor material such as amorphous silicon, or any other form of detector assembly 109 suitable for use with the type or types of illumination 106 being employed, such as X-rays. The detector elements are typically tesselated in a mosaic. The scintillator 109' converts incident photons comprising electromagnetic radiation, such as X-rays, from high-energy, high-frequency photons 106', into lower-energy, lower-frequency photons corresponding to spectral sensitivity of the detector elements, in a fashion somewhat analogous to fluorescence, as is commonly known in the context of many visible-light sources in use today. Alternatively, the detector 110 may be formed as a flat-panel array including a direct converter material such as Cadmium Zinc Telluride (CdZnTe), Mercuric Iodide (HgI$_2$), Lead Iodide (PbI$_2$), or amorphous Selenium ($\alpha$-Se).

In some modes of operation, the gantry 102 rotates the X-ray source 104 and detector 110 about an axis 116. The system 100 also includes a control module 120, which may include a motor control module 122 to control motors in the gantry 102 or to position the X-ray illumination source 104 relative to the test subject 112 and/or the detector 110.

The controller 120 includes a detector controller 124 configured to control elements within the detector 110 and to facilitate data transfer therefrom. The controller 120 also includes a drive parameter controller 128 configured to control electrical drive parameters delivered to the X-ray source 104. One or more computers 130 provide connections to the controller 120 via a bus 132 configured for receiving data descriptive of operating conditions and configurations and for supplying appropriate control signals, as will be described below in more detail with reference to Section II et seq. The computer 130 also includes a bus 134, a bus 136 and a bus 138. The bus 134 couples the computer 130 to an operator console 140.

The operator console 140 includes one or more displays 142 and an input interface 144. The input interface 144 may include user-selection tools, such as a keyboard, a mouse or other tactile input device, capability for voice commands, connections to automated computing equipment and/or other input devices. The one or more displays 142 provide video, symbolic and/or audio information relative to operation of system 100, user-selectable options and images descriptive of the test subject 112, and may include a graphical user interface for facilitating user selection among various modes of operation and other system settings.

The system 100 also includes memory devices 150, coupled via the bus 136 to the computer 130 through suitable interfaces. The memory devices 150 include mass data storage capabilities 154 and one or more removable data storage device ports 156. The one or more removable data storage device ports 156 are adapted to removably couple to portable data memories 158, which may include optical, magnetic and/or semiconductor memories and may have read and/or write capabilities, and which may be volatile or non-volatile devices or may include a combination of the preceding capabilities.

The system 100 further includes a data acquisition and conditioning module 160 that has data inputs coupled to the detector 110 and that is coupled by the bus 138 to the one or more computers 130. The data acquisition and conditioning module 160 includes analog to digital conversion circuitry for capturing analog data from the detector 110 and then converting those data from the detector 110 into digital form, to be supplied to the one or more computers 130 for ultimate display via at least one of the displays 142 and for potential storage in the mass storage device 154 and/or data exchange with remote facilities (not illustrated in FIG. 1). The acquired image data may be conditioned, as described below with reference to Section II et seq., in either the data acquisition and conditioning module 160 or the one or more computers 130 or both.

Figure 2:
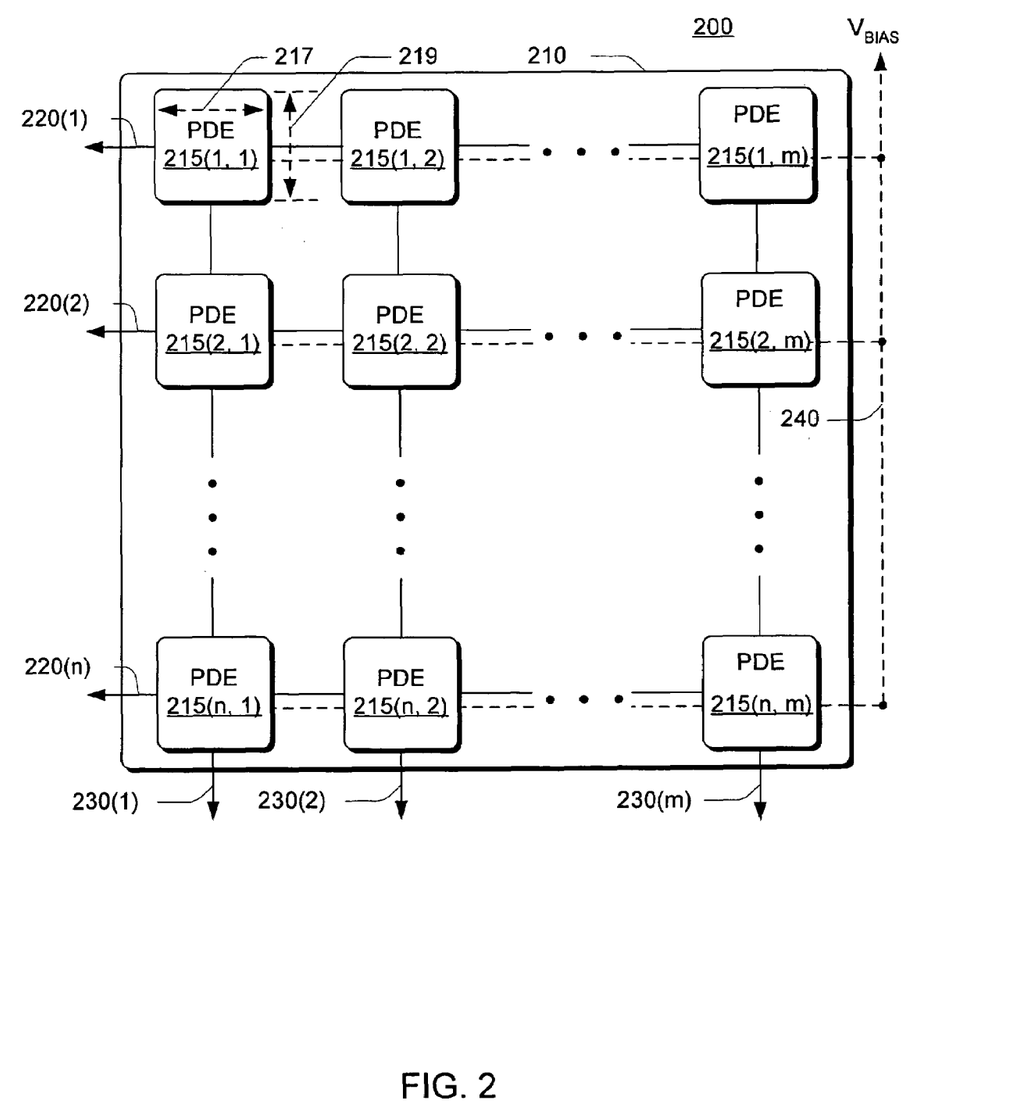
FIG. 2 is a simplified block diagram illustrating a pixelated detector system that is useful in the context of the system of FIG. 1.
Figure 3:
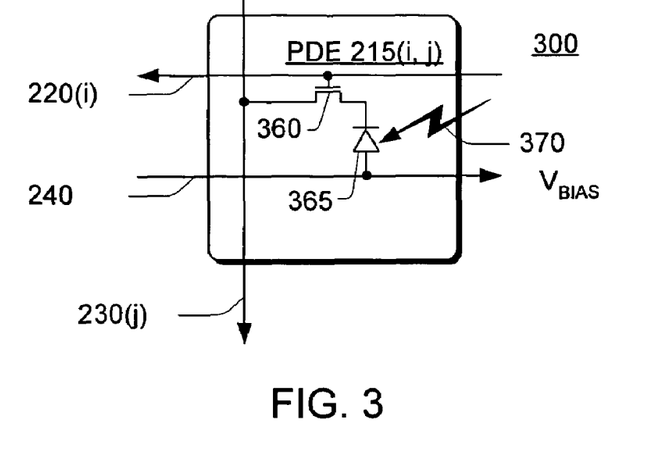
FIG. 3 is a simplified block diagram illustrating a detector element that is useful in the context of the pixelated detector system of FIG. 2.

FIG. 2 is a simplified block diagram illustrating a pixelated detector system 200 that is useful in the context of the system 100 of FIG. 1. The pixelated detector system 200 includes a detector array 210 (e.g., part of the detector 110 of FIG. 1), which in this example is assumed to be an N×M array, where N and M represent integers describing a number of rows and columns in the detector array 210. Typical detector arrays 210 include roughly 1,000 to 4,000 rows and columns. FIGS. 2 and 3 also employ "i", "j", "n" and "m" to represent integers, where i varies over a range {1, N}, and j varies over a range {1, M}.

The detector array 210 comprises a matrix or mosaic of detector elements or pixel elements, i.e., detector element PDE 215(1, 1) through detector element PDE (n, m), each having a first dimension 217 and a second dimension 219. The detector elements PDE 215 thus each have an area that is equal to a product a×b, where the first dimension 217 is represented as "a" and the second dimension 219 is represented as "b".

The detector elements PDE 215 are arranged along respective rows and columns as illustrated. For example, a series of row select lines 220(1) through 220(n) are each coupled to respective ones of detector elements PDE 215(i, j), arranged along a respective one of the row select lines 220, and a series of column signal lines ranging from a first signal column line 230(1) through a last signal column line 230(m) are each coupled to respective ones of detector elements PDE 215. In the example of FIG. 2, a suitable bias voltage $V_{BIAS}$ on bias line 240 is also coupled to each of the detector elements PDE 215. Portions of the pixelated detector system 200 of FIG. 2 and the processes discussed below in section III may be implemented as software or hardware and may comprise elements of the system 100 of FIG. 1 (supra) or the computer system 1000 of FIG. 10 (infra).

FIG. 3 is a simplified block diagram 300 illustrating a detector element PDE 215(i, j) that is useful in the context of the pixelated detector system 200 of FIG. 2. Each detector element PDE 215 includes a computer-controllable switch 360, that may be formed as a thin film amorphous silicon field effect transistor, and a detector 365 such as a diode functioning as a photo diode. The diodes 365 are fabricated to each include a relatively large photosensitive surface area (a×b, FIG. 2), ensuring that the diodes 365 are capable of intercepting a representative portion of excitation 370, responsive to illumination 106' that has passed through the test subject 112. Each diode 365 also includes relatively large capacitance, facilitating storage of electrical charge resulting from, and that is a function of, photonic excitation 370.

A cathode of each of the diodes 365 in each column 230 of the detector array 210 is connected by the source-drain conduction path of the associated transistor 360 to a common column signal line (230(1) through 230(m)) for the column. For example, the diodes 365 in column 1 are coupled to the first column signal line 230(1). An anode of each of the diodes 365 in each row 220 is connected to a common source of a negative bias voltage, $V_{BIAS}$, via the bias line 240. Respective gate electrodes of the transistors 360 in each row 220 are connected to a common row select line (220(1) through 220(n)), such as line 220(1) for row 1. The row select lines 220 and the column signal lines 230 are coupled to the detector controller 124 (FIG. 1) and the column signal lines 230 also are connected to the data acquisition and conditioning module 160.

In order to acquire an X ray image using the detector array 210, the system 100 may perform a variety of sequences. One exemplary sequence is as follows. Initially, the detector controller 124 pre-charges the detector elements 215, for example, connects all the column signal lines 230(1) through 230(m) to ground, and applies a positive voltage to all the row select lines 220(1) through 220(n). The positive voltage applied to the row select lines 220 turns ON the transistor 360 in each detector element PDE 215, placing a positive charge on the reverse biased diodes 365. Once the diodes 365 have been fully charged, the detector controller 124 applies a negative voltage, which is more negative than the negative bias voltage $V_{BIAS}$, to the row select lines 220. This negative biasing of the row select lines 220 turns OFF the transistor 360 in each detector element PDE 215 and stores a predetermined amount of charge in each of the diodes 365.

Then the detector 110 is exposed to a pulse of X-ray photons 106 produced in a conventional manner by the system illumination source 104 to generate a beam of X-ray photons 106. After traversing through the test subject 112, X-ray photons 106' are detected, either directly or by conversion to lower energy photons 370 by the scintillator 109'. When photons 370 strike the diodes 365 in the detector elements PDE 215, the diodes 365 conduct electricity and discharge a portion of their charge. The amount of discharge in a given diode 365 depends upon the relative illumination, which in turn depends upon the intensity of the X-ray energy 106' transmitted through the test subject 112. Therefore, the amount of discharge in the diode 365 in each detector element PDE 215 is a function of intensity of the incident X-rays 106' striking portions that are each optically coupled to a corresponding region, e.g., pixel or detector element PDE 215 of the X-ray detector array 210.

After termination of X-ray 106' exposure, residual charge in each diode 365 is sensed. This is done through the column signal lines which are attached to the data acquisition and conditioning module 160. The module 160 contains sensing and conversion circuitry to convert analog signals to digital or binary format to facilitate additional signal processing and conditioning, data display, data storage and/or data transmission.

Any of several types of sensing circuits can be incorporated into the data acquisition and conditioning module 160. For example, the sensing circuit can measure the voltage across the diode 365, and therefore the amount of charge remaining on the diode 365. Alternatively, the sensing circuit can connect the associated column signal lines 230(1) through 230(m) to ground potential and measure the amount of charge that is required to replace the charge removed by exposure of the respective diode 365 to photons 370.

To provide maximum image resolution, the diode 365 charges are individually sensed one row 220 at a time, via the detector controller 124 sequentially applying positive voltage to each of the row select lines 220. When a row select line 220 is positively biased, the detector array transistors 360 connected to that row select line 220 are turned ON, thereby coupling the associated diodes 365 in the selected row to their column signal lines 230(1) through 230(m) and thus to suitable signal combining and analog-to-digital conversion circuitry. The acquisition of such data is quantifiable in terms of objective characteristics that also facilitate comparison of various detectors 110, exposure parameters, metrics descriptive of resultant utility of information for analysis/diagnostic/interpretive purposes and the like, as is described below in more detail.

II. DETECTIVE QUANTUM EFFICIENCY MODEL OVERVIEW

In this section, a framework for a model descriptive of Detective Quantum Efficiency, or DQE, is developed, in a series of subsections (A) through (E). It will be appreciated that, while the model development below is phrased in terms of conventions such as Cartesian coordinates, other forms of description and other coordinate systems may be employed, without significantly altering the teachings of the present disclosure.

Aspects of modeling and characterizing performance of detectors 110 are described in U.S. Pat. No. 6,663,281 B2, entitled "X-ray detector monitoring", issued to R. Aufrichtig, P. Granfors, G. Brunst and K. Kump, which is assigned to GE Medical Systems Global Technology Company, LLC of Waukesha, Wis., and in an article entitled "Performance Of A 41×41 cm$^2$ Amorphous Silicon Flat Panel X-ray Detector Designed For Angiographic And R&F Imaging Applications", by P. Granfors, R. Aufrichtig, G. Possin, B. Giambattista, Z. Huang, J. Liu and B. Ma (Med. Phys. 30(10), October 2003, pp. 2715-2726). The model developed in this disclosure is similar to the model given in the latter publication, but is adapted for more generalized cases, viz., N'×N' or N'×M' pixel binning, and variable pixel binning. The information represented in the graphs shown in FIGS. 4 through 7 include estimates that are organized for ready application in radiographic diagnosis, rather than from the perspective of detector characterization.

II(A). INTRODUCTION TO DETECTOR PERFORMANCE CRITERIA

DQE is a measure or metric descriptive of efficiency with which a detector 110 or detector array 210 converts signals from electromagnetic radiation 106' to electrical signals. As described herein, DQE includes information that reflects comparison of a signal-to-noise ratio from that of the electromagnetic signal, e.g., 106' of FIG. 1, incident on respective photosensitive detector elements PDE 215(i, j), to a signal-to-noise ratio corresponding to electrical signals provided via the detector outputs 230. DQE is an objective measurement often employed in characterizing imaging performance of a detector 110 and in comparing relative performance aspects of different detectors 110. A general equation useful in the context of calculating DQE as a function of frequency "f" is shown below with reference to Eq. (1):

$$DQE(f) = (\Phi^*(G(\Phi)^*MTF(f))^2)/(NPS(f)), \quad \text{Eq. (1)}$$

where $\Phi$ is a parameter describing fluence of electromagnetic or other incident imaging waves 106' on detector 110, $G(\Phi)$ describes detected signal per unit of fluence, that is, a slope describing detector element PDE 215 response, MTF (f) represents a modulation transfer function applicable to the system being modeled, and NPS(f) illustrates frequency variation of an applicable noise power spectrum. If the response of the detector 110 is linear and the detector 110 produces a signal of zero when the X-ray fluence F is zero, $G(\Phi)$ may be represented by S/$\Phi$, with S representing output signal values from the detector 110. Representation of $\Phi$ as C*X, with X representing air kerma (kinetic energy released per unit mass in air), and with C representing fluence per air kerma, allows Eq. (1) to be modified as shown below in Eq. (2):

$$DQE(f) = ((S^*MTF(f))^2)/(NPS(f)^*X^*C). \quad \text{Eq. (2)}$$

II(B). BINNED IMAGING MODES

A common pixelated medical imaging detector array 210 realization employs amorphous silicon as a semiconductive and photoconductive material, as is described in more detail with reference to FIG. 3. Detector arrays 210 so formed include an array of detector elements PDE 215, connected to respective gate lines 220 and respective data lines 230, typically arranged according to a Cartesian coordinate system, often with the gate lines 220 orthogonal to the data lines 230. When a gate line 220 is switched to a suitable voltage to read out data from the detector elements PDE 215 via respective data lines 230, signals from all of the detector elements PDE 215 on that gate line 220 are sensed by suitable circuitry coupled to each of the data lines 230. Binned modes of operation are facilitated by control circuitry, for example in the detector controller 124 of FIG. 1, which may be physically contained with the detector 110, that permit combining signals from multiple neighboring detector elements PDE 215 to provide a larger pixel. This is achieved by reading out multiple gate lines 220 simultaneously and summing data signals from multiple data lines 230. When a number N' of the gate lines 220, and a number M' of the data lines 230 are coordinated in this fashion, this is called binning of N' by M' pixels. When N'=M'=1, the detector array 210 is read out at full resolution.

In some applications, less than all of the detector elements PDE 215 in the detector array 210 are involved in providing data employed to derive an image. For example, in some applications, a central portion of the detector array 210 is selectively employed to provide high-resolution imaging of particularized conditions. Angiography and fluoroscopy exemplify applications where a subset of the detector elements PDE 215 in the detector array 210 may be used to form an image while other detector elements are not used to make the image In one embodiment, a detector array 210 may include 2048×2048 detector elements PDE 215, but, in some situations, only employ 1024×1024 detector elements PDE 215 within a larger array, such as a central group of those detector elements PDE 215, responsive to machine-executable instructions and as appropriate to the imaging procedure being initiated. As a result, increased flexibility of operation coupled with reduced mechanical complexity may be realized.

II(C). COMPUTING DOE IN BINNED MODES

The MTF(f) function may be usefully treated as a product of at least two components, with one of these components representing a scintillator portion (descriptive of the MTF of the light incident to the detector array 210) and another of these components representing an aperture component, A(x, y), providing information demonstrative of the sensitivity of the detector array 210. The aperture component A(x, y) may be approximated as shown below in Eq. (3), with reference to a Cartesian coordinate system employing axes X and Y:

$$A(x,y)=X(x)*Y(y). \quad \text{Eq. (3)}$$

The scintillator component and the aperture component A(x, y) collectively describe aspects of the responsivity of the detector 110. Of these two representative components, only the aperture component of the MTF changes significantly when the detector array 210 readout is modified from full-resolution mode (i.e., measuring output signals from each detector element individually) to binned modes, where an integer number, represented as N'×M', of such detector element output signals, such as two or more, are combined in formation of a non-destructively derived imaging representation.

As an example, an aperture for N'×M' binned mode of operation of the detector array 210 may be usefully modeled as an aperture of a full-resolution imaging mode, replicated N'×M' times. Employing the approximation of Eq. (3) permits description of detector performance vs. binning as described below.

In at least this context, and utilizing applicable Fourier techniques (as described, for example, in (Med. Phys. 30(10), October 2003, pp. 2715-2726 at p. 2719), a modulation transfer function applicable to binned modes of operation of a detector array 210, wherein the binning has N' detector elements PDE 215 along one axis and M' detector elements PDE 215 along another axis, may be computed from the MTF in full resolution mode as shown below with reference to Eq. (4):

$$MTF(u,v)_{N'\times M'}=((\sin(\pi puN')*(\sin((\pi pvM'))*(MTF_{1\times 1}(u,v))/(N'*\sin(\pi pu)*M'*\sin(\pi pv)), \quad \text{Eq. (4)}$$

where "p" describes pixel pitch within the detector array 210 and "u" and "v" represent Cartesian coordinates in frequency space.

The dependence of NPS(f) on imaging mode is somewhat more complex to model mathematically, owing to effects due to aliasing, which, in turn, are responsive to spatial sampling, among other things, and particularly with respect to the Nyquist theorem, as is well-known to those of skill in the relevant arts. Absent electronic noise, NPS(f) also includes scintillator and aperture effects, each including noise aliased from frequencies above the Nyquist frequency. As a result, even though the scintillator component does not change, the scintillator component of NPS(f) differs significantly between modes of detector sampling, at least in part because of differences in aliasing effects.

In a fashion analogous to that described above with respect to transformation of the MTF(f) function (Eq. (4)), a "pre-sampling" NPS(f) representation is usefully modeled as a product of aperture and scintillator components. As a practical matter, measured NPS(f) values are well approximated by summing such "pre-sampling" NPS(f) over applicable aliases. Simplifying the aperture component A(x, y) of the MTF(f) via employment of separable products of sinc functions (i.e., sin(x)/x), the NPS(f) function, in full-resolution and binned modes, may be written as:

$$NPS_{1\times 1} = \sum_{m,n=-\infty}^{\infty} \left\{ \left[ \frac{\sin(\pi a(u+m/p))}{\pi a(u+m/p)} \right]^2 \left[ \frac{\sin(\pi b(v+n/p))}{\pi b(v+n/p)} \right]^2 F(u+m/p, v+n/p) \right\}, \text{ and} \quad \text{Eq. (5)}$$

$$NPS_{N'\times M'} = \sum_{m,n=-\infty}^{\infty} \left[ \frac{\sin(\pi pN'(u+n/N'p))}{N'\sin(\pi p(u+nl/(N'p)))} * \frac{\sin(\pi pM'(v+m/(M'p)))}{M'\sin(\pi p(v+ml/(M'p)))} \right]^2 * \left[ \frac{\sin(\pi a(u+n/(N'p)))}{\pi a(u+n/(N'p))} \right]^2 * \left[ \frac{\sin(\pi b(v+m/(M'p)))}{\pi b(v+m/(M'p))} \right]^2 * F(u+n/(N'p), v+m/(M'p)). \quad \text{Eq. (6)}$$

Here "a" and "b" represent dimensions of the photosensitive elements PDE 215, as illustrated in FIG. 2, "m" and "n" represent integer variables, and F represents a function descriptive of the scintillator portion of the "pre-sampling" NPS. F, in turn, may be parameterized as a generalized two-dimensional Lorentzian function, an example of which is shown in Eq. (7) below:

$$F(u,v)=\gamma/[(1+\alpha(u^2+v^2)]^\beta, \quad \text{Eq. (7)}$$

where the parameter γ represents NPS(f), evaluated at zero frequency. Substituting Eq. (7) into Eq. (5) and varying values of "α" and "β" in order to fit measured values obtained for NPS(f), where the measured values are obtained in the full-resolution mode, allows detector 110 performance to be modeled. When the α and β values that are found to fit the measured NPS properties are substituted into Eq. (7), the result may be employed to predict NPS functions corresponding to operation of the detector 110 in various binned modes. Combining Eqs. (4) through (7) allows prediction of DQE(f) applicable to various binned modes of operation, from data measured in full-resolution mode.

II(D). COMPUTING DQE(F) VERSUS EXPOSURE (DOSE) FOR BINNED MODES

Expected DQE(f) at lower exposures can be predicted from the measured high exposure DQE(f) by decomposing the NPS into a frequency-dependent quantum noise component, $NPS(f, X) = X*NPS_{qX}(f)$, that is proportional to exposure, and a system component, $NPS_0$, that is independent of frequency and exposure. A representation resulting from such treatment is given below in Eq. (8):

$$NPS(f,X) = X*NPS_{qX}(f) + NPS_0. \quad \text{Eq. (8)}$$

The expression shown in Eq. (8) may be substituted into that shown in Eq. (2). A result of such substitution is shown below in Eq. (9):

$$DQE(f,X) = S^2 * MTF^2 / [C^* X^2 (NPS_{qX} + NPS_0/X)]. \quad \text{Eq. (9)}$$

At high exposures, $NPS_0/X$ is negligible in comparison to $NPS_{qX}$. As a result, Eq. (9) may be simplified to provide the expression shown below in Eq. (10):

$$DQE(f, X) = DQE_{highX}(f)/[1 + NPS_0/(X * NPS_{qX}(f))] = \quad \text{Eq. (10)}$$
$$DQE_{highX}(f) * [X * NPS_{qX}(f)/(NPS_0 + (X * NPS_{qX}(f)))],$$

where $DQE_{highX}(f)$ represents the DQE in the high exposure limit. Eq. (10) shows that the DQE at exposures below the high exposure extreme $DQE_{highX}(f)$ decreases from that high exposure limit by a factor equal to a ratio of quantum noise to total noise.

System noise is described by $NPS_0$ and may be further decomposed into a noise contribution, $NPS_{pixel}$, arising from each pixel or detector element PDE 215 in the detector array 210, and noise arising from data-line and digitization sources, represented as $NPS_{line}$. Substitution of these expressions into Eq. (10) allows that to be expressed as shown below in Eq. (11):

$$NPS_{0,N'xM'} = N'*M'*NPS_{pixel} + M'*NPS_{line}. \quad \text{Eq. (11)}$$

The data acquisition and conditioning module 160 of FIG. 1 determines appropriate binning of signals from the detector elements PDE 215 and the system 100 is capable of configuring the detector array 210 to operate in that binning mode via suitable control signals. For a $DQE_{highX}(f)$ corresponding to given detector 110, desirable binning parameters at relatively low exposure can be determined by treating DQE(f, X) appropriately, where the detector entrance exposure, X, is directly proportional to the average image signal that has been acquired, for example via the data acquisition circuitry 160 of FIG. 1. The average may be computed in a statically robust way, e.g., by computing median or threshold values, and/or by excluding anomalous results, or "outliers" (such as anomalously high or low values), prior to computing the average. The calculated average is then converted into an entrance exposure by accounting for a selected detector gain setting.

II(E). DQE ESTIMATES FOR DIFFERENT BINNING MODES

FIGS. 4 through 7 are graphs illustrating detective quantum efficiency variation as a function of exposure for different binning configurations and exposure conditions that are useful in the context of the system of FIG. 1. Other estimates may be derived by employing the theoretical outlines developed in the preceding subsections. FIGS. 4 through 7 show computed DQE as a function of exposure at the detector 110, spatial frequency, and amount of binning, for selected examples. The concepts described in this disclosure use this type of information to choose an appropriate amount of binning for the imaging task. This choice may be made by the operator or by the system 100, and may be either static or dynamic, i.e., adapted during the imaging as, for example, during a fluoroscopic imaging sequence.

FIGS. 4 through 7 depict graphs 400 through 700, respectively, each having an abscissa calibrated to represent dose (in microRoentgens or μR) as an independent variable and an ordinate calibrated to represent DQE as a dependent variable. Each of FIGS. 4 through 7 provides five examples, correspond respectively to 1×1, 2×2, 3×3, 4×4 and 5×5 binning of signal data from the detector array 210, with each trace having a parenthetical suffix corresponding to the binning mode being modeled, as noted in the tabular entries presented with each graph.

Figure 4:
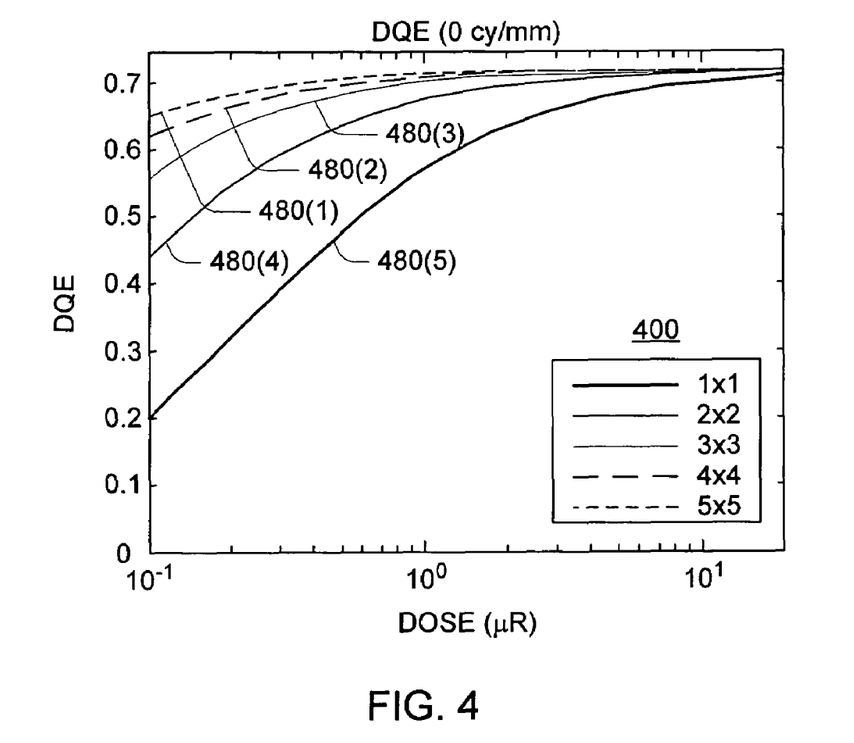
FIGS. 4 through 7 are graphs illustrating computed estimates of detective quantum efficiency variation as a function of exposure for different binning configurations and exposure conditions, which graphs find utility in the context of the system of FIG. 1.
Figure 5:
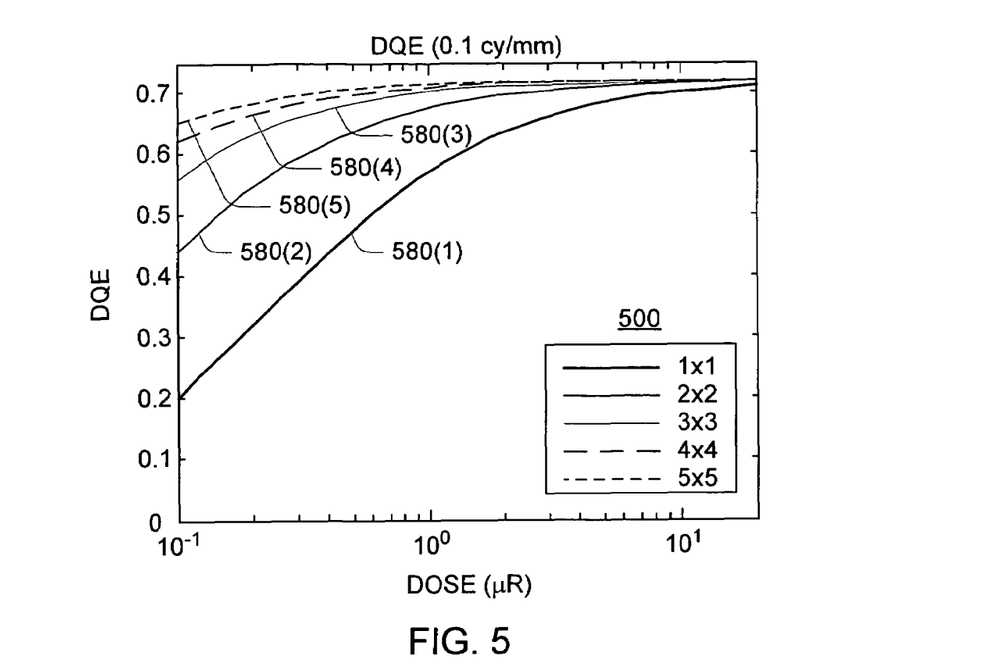
Figure 6:
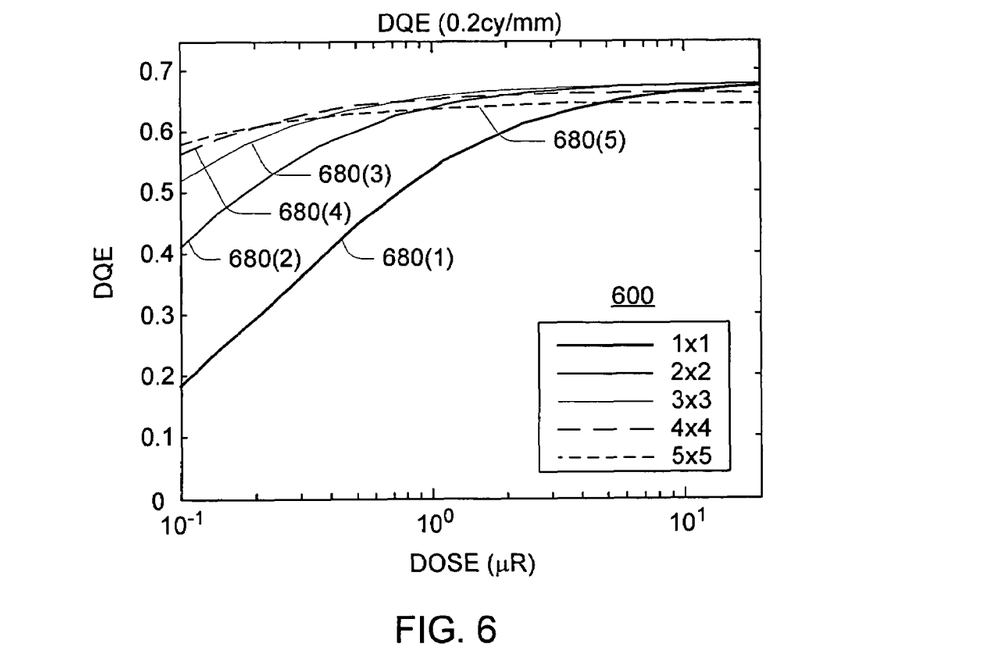
Figure 7:
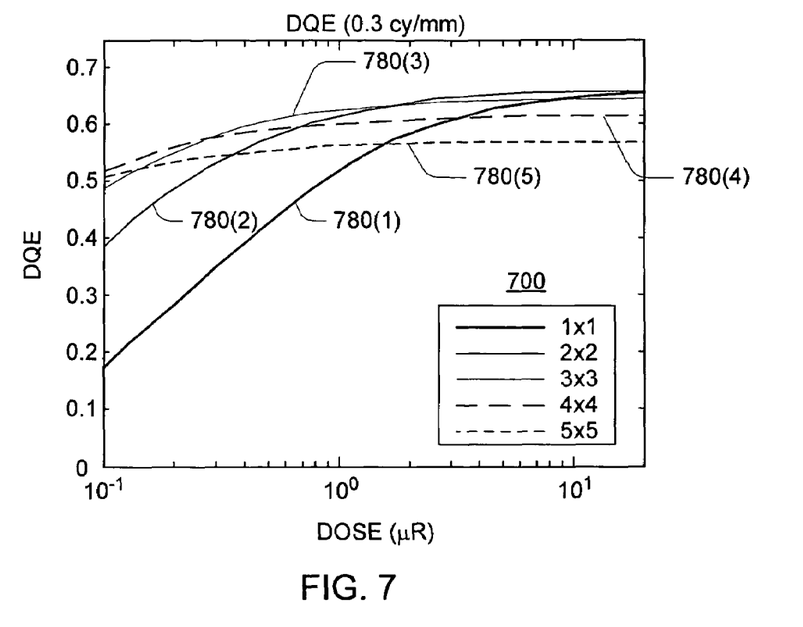

FIG. 4 represents five examples 480(1), 480(2), 480(3), 480(4) and 480(5), for exposure conditions corresponding to a spatial frequency of zero cycles per millimeter. FIG. 5 represents five examples 580(1), 580(2), 580(3), 580(4) and 580(5), for exposure conditions corresponding to a spatial frequency of one-tenth cycle per millimeter. FIG. 6 represents five examples 680(1), 680(2), 680(3), 680(4) and 680(5), for exposure conditions corresponding to a spatial frequency of two-tenths cycle per millimeter. FIG. 7 represents five examples 780(1), 780(2), 780(3), 780(4) and 780(5), for exposure conditions corresponding to a spatial frequency of three-tenths cycle per millimeter. The models described above may be usefully employed, together with empirical data and the examples of FIGS. 4 though 7, to provide estimates useful in balancing dose, spatial frequency response, DQE and other variables in selecting one or more candidate binning modes and corresponding exposure parameters useful for a particular imaging task and test subject 112. Interpolation may be employed for estimation of other scenarios, and the models described herein, as well as historical data, may also be used in arriving at a set of candidate modes for imaging consideration.

One or more desirable levels of binning can be determined, for example via a look-up table that represents the information of the graphs shown in FIGS. 4 through 7, where the look-up table is contained in the memory systems 150 of the computer 130 of FIG. 1, for example. Comparison of the several cases for which estimates are provided in FIGS. 4 through 7 illustrates this process. For example, using 0 cy/mm together with a calculated entrance exposure of 0.5 μR, a 4×4 binning may be preferred, with negligible added benefit resulting from 5×5 binning. The system 100 of FIG. 1 can also be set for a slightly higher spatial frequency, e.g. at 0.3 cy/mm, where binning in a 3×3 binning mode provides useful imaging properties.

Benefits obtained via DQE considerations coupled with binning, together with careful binning selection, are particularly important at low exposures. In dose-starved situations, there is very little high spatial frequency content in resulting image data, and low spatial frequency content is correspondingly significant in forming an image having useful diagnostic properties. The benefits of combining signals from multiple detector elements PDE 215 or pixels often provides larger increases in resultant image quality, compared to non-binning approaches or in some very simple binning cases (such as 2×2 binning). The benefits of variable multi-element signal binning accrue in exactly this imaging situation, viz., one of low exposure and where low spatial frequency imaging data are significant in diagnosis, for example.

Process embodiments of these strategies for providing diagnostically-useful images together with benefits associated with variable binning of detector data are described below in more detail with reference to FIGS. 8 and 9.

III. PROCESS EMBODIMENTS

In the previous section, an overview of models and techniques for variable binning of detector data in medical imaging was described. In this section, the models of that section are used in describing the operation of a series of embodiments, with the particular processes of such embodiments being described by reference to relevant flowcharts. Describing the processes by reference to one or more flowcharts enables one skilled in the art to develop programs, firmware, or hardware, including such instructions to effectuate the processes through one or more processors responsive to computer-readable instructions embodied on computer-readable media.

These capacities are often accomplished using suitable computers, including one or more processors, by executing the instructions embodied in articles of manufacture such as computer-readable media, or as modulated signals embodied in a carrier wave. As a result, the computer-readable instructions may include capacity for accepting revised computer-readable information descriptive of revised capabilities, which may relate to revisions of aspects of the system 100 via substitution of components, revisions of data-processing structures and the like. Similarly, processes performed by server computer programs, firmware, or hardware also are represented by computer-executable instructions. The processes of the present disclosure are performed by one or more program modules executing on, or performed by, firmware or hardware that is a part of a computer (e.g., computer 130, FIG. 1).

In some embodiments, processes disclosed herein are implemented as a computer data signal embodied in a carrier wave, that represents a sequence of instructions which, when executed by one or more processors, such as a processor contained in or associated with the computer 130 in FIG. 1, causes the respective process to occur. In other embodiments, the processes disclosed herein are implemented as a computer-accessible medium having executable instructions capable of directing a processor, such as a processor contained in or associated with the computer 130 in FIG. 1, to perform the respective process. In varying embodiments, the medium is a magnetic medium, an electronic medium, or an electromagnetic/optical medium.

More specifically, in a computer-readable program embodiment, programs can be structured in an object-orientation using an object-oriented language such as Java, Smalltalk or C++, and the programs can be structured in a procedural-orientation using a procedural language such as COBOL or C. Software components may communicate in any of a number of ways that are well-known to those skilled in the art, such as application program interfaces (API) or interprocess communication techniques such as remote procedure call (RPC), common object request broker architecture (CORBA), Component Object Model (COM), Distributed Component Object Model (DCOM), Distributed System Object Model (DSOM) and Remote Method Invocation (RMI). The components execute on as few as one computer as in computer 130 in FIG. 1, or on multiple computers.

Figure 8:
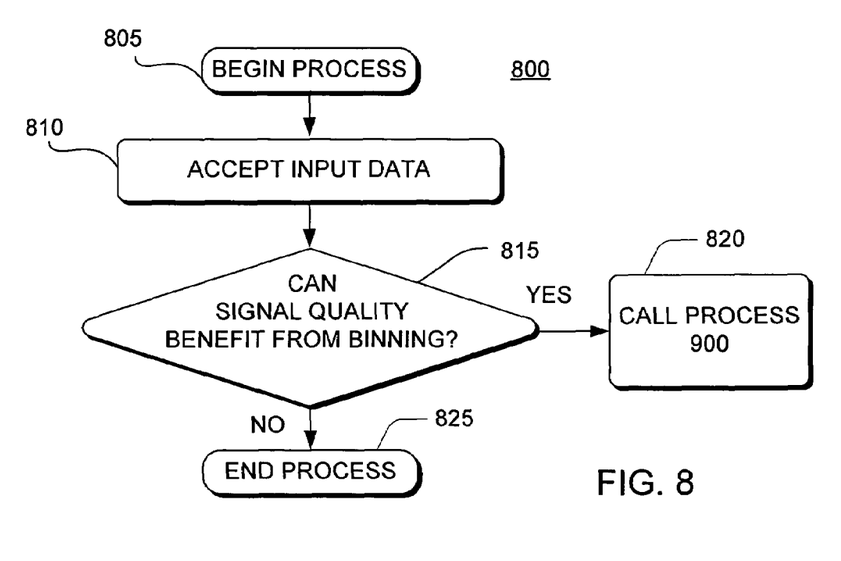
FIG. 8 shows a flowchart describing an imaging process that finds utility in the system of FIG. 1.

FIG. 8 shows a flowchart describing an imaging process 800 for determining estimated image quality versus binning at a specified dose that finds utility in the system 100 of FIG. 1. The process 800 begins in a block 805.

In a block 810, the process 800 accepts input data descriptive of a type of imaging task to be performed, for example, angiographic study, examination of hard tissue (such as bone), pulmonary organ study, fluoroscopy or other non-destructive imaging or diagnostic characterization, and also incorporating data descriptive of the test subject 112 under study, such as thickness, weight, and other variables relevant to the imaging process. Input data such as dose and voltage may also be provided. Control then passes to a query task 815.

In query task 815, the input data and information descriptive of capabilities of the system 100 are incorporated to provide one or more suggested exposure regimes likely to be consistent with noise and signal parameters desired, the type of imaging sought, the kinds of diagnostic criteria to be extracted from resultant data and the like. Among other things, the query task 815 includes determination of when binning of larger numbers of pixels, that is, binning of pixels in groups larger than 2×2, or an extended group of pixels, may result in benefits, such as reduction of dose, coupled with appropriate resolution and contrast.

When the query task 815 determines that binning of larger numbers of pixels may provide desirable characteristics consistent with capabilities of the system 100 and conditions relevant to the test subject 112 as well as the type of characterization being contemplated, control passes to a block 820. In the block 820, a process 900 is invoked, as described below with reference to FIG. 9.

When the query task 815 determines that conventional exposure and data collection procedures are appropriate for the imaging and diagnostic desires being undertaken, control passes to a block 825. In the block 825, the process 800 terminates and imaging proceeds in a conventional manner.

Figure 9:
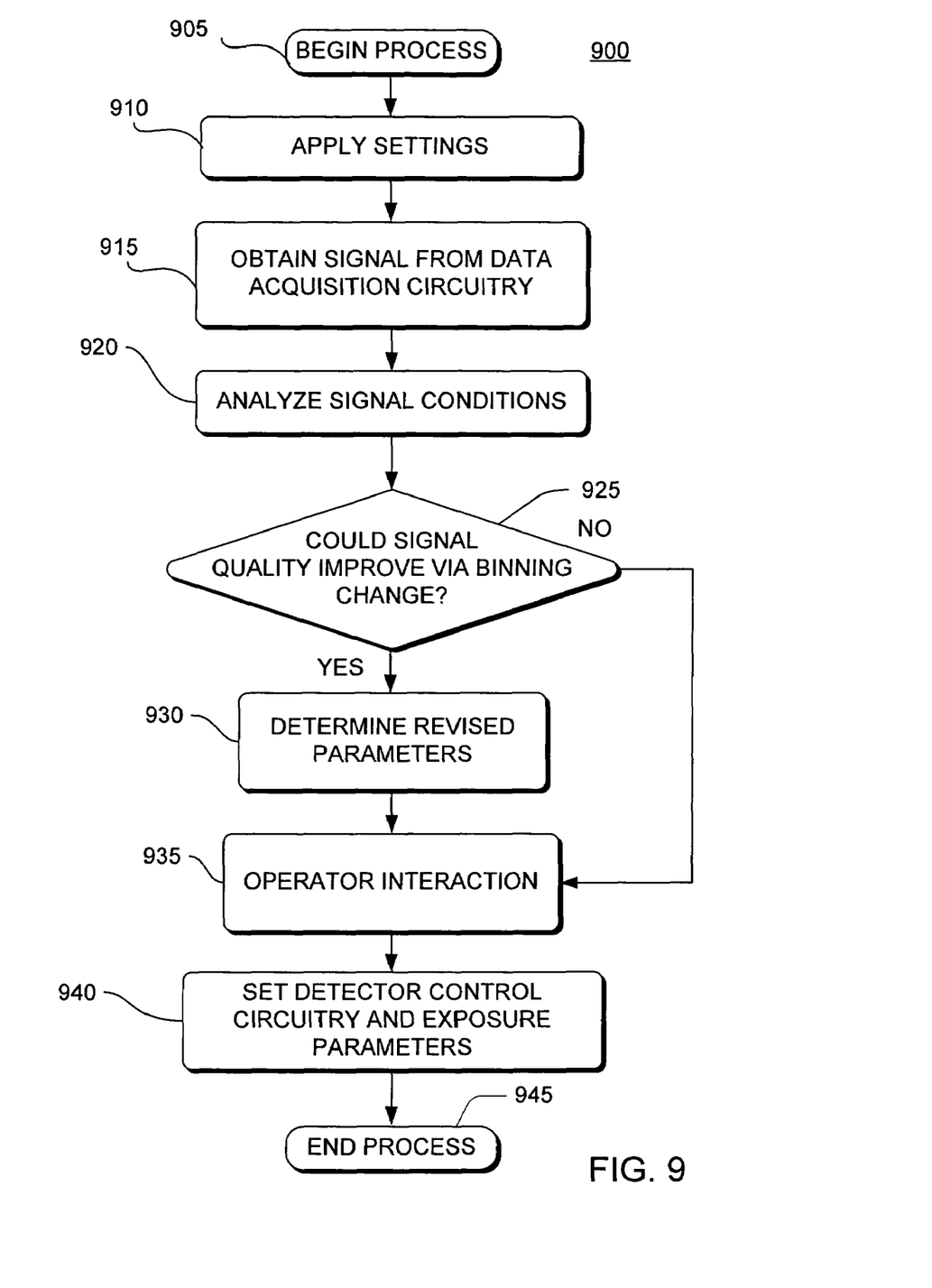
FIG. 9 shows a flowchart describing a variable pixel binning process that finds utility in the system of FIG. 1.

FIG. 9 shows a flowchart describing a variable pixel binning process 900 that finds utility in the system 100 of FIG. 1. The process 900 begins in a block 905.

In a block 910, the process 900 employs settings specified for the type of imaging procedure presently relevant, as well as information descriptive of the test subject 112 (e.g., as noted with respect to the block 810 supra), together with a range of capabilities of the system 100 being employed, in contemplation of a set of appropriate exposure and data collection regimes. Control then passes to a block 915.

In the block 915, signal conditions relative to the detector 110, data collection and processing regimes, and exposure conditions are collected. In one embodiment, signal conditions may be derived from historical data, look-up tables and the like, for substantially similar tasks and conditions. In one embodiment, signal conditions may include one or more frames of imaging signal information responsive to an exposure of X-rays 106' that have passed through the test subject 112. Control then passes to a block 920.

In the block 920, the process 900 analyzes the ensemble of factors specific to the present imaging task against the backdrop of information descriptive of signal conditions. In part, the block 920 sorts the information to select and rank order data relevant to the type of imaging and test subject 112 of present interest. Control then passes to a query task 925.

In the query task 925, the process 900 determines when signal quality (such as DQE), coupled with dose considerations relative to the test subject 112, may offer benefits via binning of larger numbers of pixels, in contrast to conventional imaging methodologies. When the query task 925 determines that benefits may be obtained via the techniques described in this disclosure, control passes to a block 930. When the query task 925 determines that benefits are unlikely to be obtained via the techniques described in this disclosure, control passes to a block 935.

In the block 930, the process 900 determines revised parameters for configuration of the system 100. The determination of the block 930 may include one or more binning regimes likely to prove useful, one or more exposure settings associated with each of the binning regimes, and the like.

For example, a feedback loop may be incorporated that changes the voltage and current to the illumination source or x-ray tube 104, and the feedback loop may switch filters in and out of the beam 106, 106', to present a high quality image to the clinician, together with reduced dose to the test subject 112. The feedback loop is automatically implemented by the system 100, based on analysis of the image and other factors. When the image can be improved by changing the binning mode, or when the image quality may be maintained but require a reduced dose via modification of the binning mode, the system 100 alters the exposure and data collection parameters automatically. The clinician is always presented with the best image that the system 100 is capable of, at the lowest dose to the test subject 112. Control then passes to the block 935.

In the block 935, data relative to the exposure and data collection methodologies described above are made available to a system operator. For example, the display 142 may provide information descriptive of one or more exposure and data collection regimes to the operator. As another example, the operator may over-ride that regime or regimes offered by the processes 800 and 900 via entry of suitable commands, such as commands selected using the input media 144. The data associated with the block 935 facilitate rank-ordering of exposure and data-collection options that are consistent with the system 100, the test subject 112, and other relevant factors. Affirmative selection of an exposure regime may be sought from the operator prior to exposure of a test subject 112 that is a living being, in the block 935, however, selection of an exposure regime may also be effectuated automatically. Control then passes to a block 940.

In the block 940, the system 100 is configured to operate in conformance with selected criteria. Control then passes to a block 945, ending the process 900 and initiating operation of the imaging system 100 as determined via processes 800 and 900, among other things. The processes 800 and 900 may be implemented as hardware or software or a combination thereof, and may be updated via addition or substitution of machine-readable and executable instructions, as is described below in more detail with reference to FIG. 10.

IV. HARDWARE AND OPERATING ENVIRONMENT

Figure 10:
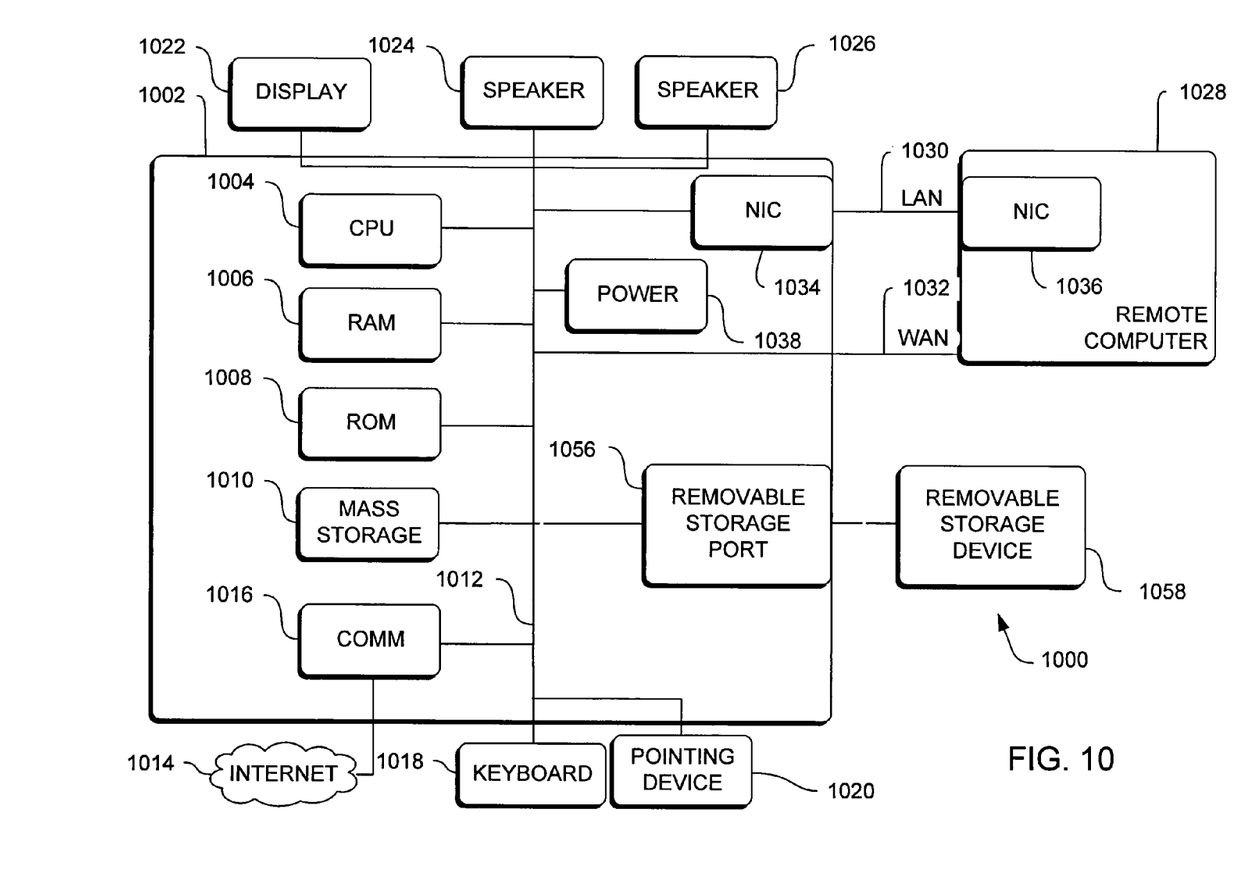
FIG. 10 is a block diagram of a hardware and operating environment in which different embodiments can be practiced.

FIG. 10 is a block diagram of a hardware and operating environment 1000, including one or more computers 1002, in which different embodiments can be practiced. The description of FIG. 10 provides an overview of computer hardware and a suitable computing environment in conjunction with which some embodiments can be implemented. Embodiments are described in terms of a computer executing computer-executable instructions. However, some embodiments can be implemented entirely in computer hardware in which the computer-executable instructions are implemented in read-only memory. Some embodiments can also be implemented in client/server computing environments where remote devices that perform tasks are linked through a communications network. Program modules can be located in both local and remote memory storage devices in a distributed computing environment.

The computer 1002 includes one or more processors 1004, commercially available from Intel, Motorola, Cyrix and others. The computer 1002 also includes random-access memory (RAM) 1006, read-only memory (ROM) 1008, and one or more mass storage devices 1010, and a system bus 1012, that operatively couples various system components to the processing unit 1004 and/or to each other and/or external apparatus. The memories 1006 and 1008, and the mass storage devices 1010, are types of computer-accessible media. Mass storage devices 1010 are more specifically types of nonvolatile computer-accessible media and can include one or more hard disk drives, floppy disk drives, optical disk drives, and tape cartridge drives. The processor 1004 executes computer programs stored on these various computer-accessible media.

The computer 1002 can be communicatively connected to the Internet 1014 via a communication device 1016. Internet 1014 connectivity is well known within the art. In one embodiment, a communication device 1016 is a modem that responds to communication drivers to connect to the Internet via what is known in the art as a "dial-up connection." In another embodiment, the communication device 1016 includes an Ethernet® or similar hardware network card connected to a local-area network (LAN) that itself is connected to the Internet 1014 via what is known in the art as a "direct connection" (e.g., T1 line, etc.).

A user may enter commands and information into the computer 1002 through input devices such as a keyboard 1018 or a pointing device 1020. The keyboard 1018 permits entry of textual information into computer 1002, as known within the art, and embodiments are not limited to any particular type of keyboard 1018. The pointing device 1020 permits the control of the screen pointer provided by a graphical user interface (GUI) of operating systems such as versions of the Microsoft Windows® operating system. Embodiments are not limited to any particular pointing or tactile input device 1020. Such pointing devices 1020 include mice, touch pads, trackballs, remote controls and point sticks. Other input devices (not shown) can include a microphone, joystick, game pad, satellite dish, scanner, or the like.

In some embodiments, the computer 1002 is operatively coupled to a display device 1022 via the system bus 1012. The display device 1022 permits the display of information, including computer, video and other information, for viewing by a user of the computer 1002. Embodiments are not limited to any particular display device 1022, which may include cathode ray tube (CRT) displays (monitors), as well as flat panel displays such as liquid crystal displays (LCD's). In addition to a monitor 1022, computers 1002 typically include other peripheral input/output devices such as printers (not shown). Speakers 1024 and 1026 may provide audio output signals, responsive to commands delivered through the system bus 1012.

The computer 1002 also includes an operating system (not shown) that is stored on the computer-accessible media RAM 1006, ROM 1008, and mass storage device 1010, that is accessed and executed by the processor 1004. Examples of operating systems include the Microsoft Windows®, Apple MacOS®, Linux® and UNIX® operating systems. Examples are not limited to any particular operating system, however, and the construction and use of such operating systems are well known within the art.

Embodiments of the computer 1002 are not limited to any type of computer 1002. In varying embodiments, the computer 1002 comprises a PC-compatible computer, a MacOS® operating system compatible computer, a Linux® operating system compatible computer, or a UNIX® operating system compatible computer. The construction and operation of such computers are well known within the art.

The computer 1002 can be operated using at least one operating system to provide a graphical user interface (GUI) including a user-controllable pointer. The computer 1002 can have at least one web browser application program executing within at least one operating system, to permit the computer 1002 to access an intranet, extranet or Internet 1014 world-wide-web pages as addressed by Universal Resource Locator (URL) addresses. Examples include the Netscape Navigator® and the Microsoft Internet Explorer® browser programs.

The computer 1002 can operate in a networked environment using logical connections to one or more remote computers, such as a remote computer 1028. These logical connections are achieved by a communication device coupled to, or forming a part of, the computer 1002. Embodiments are not limited to a particular type of communications device. The remote computer 1028 can be another computer, a server, a router, a network PC, a client, a peer device or other common network node. The logical connections depicted in FIG. 10 include a local-area network (LAN) 1030 and a wide-area network (WAN) 1032. Such networking environments are commonplace in offices, enterprise-wide computer networks, intranets, extranets and the Internet 1014.

When used in a LAN-networking environment, the computer 1002 and remote computer 1028 are connected to the local network 1030 through network interfaces or adapters 1034, which is one type of communications device 1016. The remote computer 1028 also includes a network device 1036. When used in a conventional WAN-networking environment, the computer 1002 and remote computer 1028 communicate with a WAN 1032 through one or more modems (not shown). The modem, which can be internal or external, is connected to the system bus 1012. In a networked environment, program modules depicted relative to the computer 1002, or portions thereof, can be stored in the remote computer 1028.

The computer 1002 also includes a power supply 1038. Each power supply 1038 can be a battery. The computer 1002 also may include a removable memory storage port 1056 capable of accepting a removable data storage device 1058 (analogous to the port 156 and removable data storage device 158 of FIG. 1), which provides capability for revision of machine-readable instructions, among other things. Computer-readable instructions and/or data may also be supplied to the computer 1020 via coupling to a suitably-programmed removable data storage device 1058 and/or via a carrier wave including modulation of computer-readable information coupled from external sources, such as the Internet 1014 or other external interconnections.

The computer 1002 may function as one or more of the control segments of module 120 (FIG. 1), the computer 130, the operator console 140 and/or the data acquisition and conditioning module 160, for example, via implementation of the processes 300, 400, 500 and 600 of FIGS. 3 through 6 as computer program modules.

V. CONCLUSION

A computer-based medical imaging system is described. Although specific embodiments have been illustrated and described herein, it will be appreciated by those of ordinary skill in the art that any arrangement which is calculated to achieve the same purpose may be substituted for the specific embodiments shown. This disclosure is intended to cover any adaptations or variations. For example, although described in procedural terms, one of ordinary skill in the art will appreciate that implementations can be made in a procedural design environment or any other design environment that provides the required relationships.

In particular, one of skill in the art will readily appreciate that the names or labels of the processes and apparatus are not intended to limit embodiments. Furthermore, additional processes and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future communication devices, different file systems, and new data types. The terminology used in this disclosure is meant to include all object-oriented, database and communication environments and alternate technologies which provide the same functionality as described herein.

What is claimed is:

1. A process for variable binning of detector data in a non-destructive imaging system, comprising:
   receiving input data indicative of a desired image quality;
   receiving input data indicative of an imaging task;
   receiving input data describing a test subject or a portion of the test subject;
   combining the received input data about desired imaged quality, imaging task, and test subject with non-destructive imaging system capabilities;
   determining if the non-destructive imaging system is capable of achieving the image quality goals using binning, wherein the capability is a reduction of one or more dose, spatial frequency response, detective quantum efficiency and other user defined variables; and
   performing binning analyses when the non-destructive imaging system is capable of achieving the image quality goals using binning.

2. The process of claim 1, wherein the act of determining comprises an act of determining a dose of X-radiation consistent with binning and dose reduction.

3. The process of claim 1, wherein the act of determining includes an act of estimating detective quantum efficiency, and further comprising an act of selecting among full resolution mode, two by two binning, three by three binning, four by four binning and five by five binning for at least a portion of a detector array.

4. The process of claim 1, wherein the act of determining includes estimating detective quantum efficiency and dose, and further comprising, after determining, an act of configuring a detector array to employ fewer than all detector elements in the detector array.

5. The process of claim 1, further comprising an act of estimating detective quantum efficiency, image quality, dose and contrast for a plurality of detector array operation modes including one or more of: full resolution imaging, full field of view, two by two binning, three by three binning, four by four binning and five by five binning, and further comprising distinguishing those among the estimated modes that are capable of meeting predetermined image quality goals.

6. The process of claim 1, wherein the act of determining further includes an act of estimating detective quantum efficiency.

7. The process of claim 1, further including acts of:
configuring an X-ray detector array in response to the act of determining;
analyzing data from the configured X-ray detector array; and
modifying configuration of the X-ray detector responsive to the act of analyzing.

8. A non-destructive imaging system, comprising:
an illumination source configured to internally illuminate a test subject;
a detector array including a tesselation of detector elements aligned with the illumination source opposite the test subject, each detector element corresponding to a pixel in a full resolution imaging mode of the detector array;
a controllable driver coupled to the detector array and cooperatively facilitating capability for multiple functionality settings for a detector array, including binning of more than four pixels;
an interface capable of accepting input data indicative of image quality goals and facilitating selection of at least one of the multiple functionality settings;
a processor coupled to the interface;
a storage device coupled to the processor and having software operative on the processor for:
determining if the detector array is capable of achieving the image quality goals using binning, wherein the capability is a reduction of one or more dose, spatial frequency response, detective quantum efficiency and other user defined variables; and
performing binning analyses when the detector array is capable of achieving the image quality goals using binning.

9. The system of claim 8, further comprising:
the software operative on the processor for
estimating detective quantum efficiency for several of the multiple detector array functionality settings;
distinguishing among the several based on dose and image quality goals to provide one or more candidate functionality settings; and
selecting one of the candidate functionality settings.

10. The system of claim 8, wherein the illumination source comprises an X-ray illumination source and the detector elements include semiconductive material, each detector element being associated with a switch coupled to the controllable driver.

11. The system of claim 8, wherein the controllable driver is configured to selectively group the detector elements into one of a menu of extended groups, and further comprising a control and signal processing module configured to:
combine signals from detector elements within each extended group defined by the controllable driver; and
provide digital signals representative of data from each of the extended groups.

12. The system of claim 8, wherein the illumination source includes an X-ray illumination source, and further comprising a control module configured to facilitate operation of the system in conformance with one or more of: full resolution imaging, full field of view imaging, two by two binning, three by three binning, four by four binning or five by five binning, and further comprising capability for distinguishing those among the estimated modes that are capable of meeting predetermined image quality goals.

13. The system of claim 8, wherein the illumination source includes an X-ray illumination source, and wherein the system further includes stored data descriptive of empirical characterization of the system as well as calculated data useful in rank-ordering of detector array functionality settings in conformance with identified characteristics of the test subject and goals associated with an imaging task relative to the test subject.

14. The system of claim 8, wherein the system further includes stored data descriptive of calculated estimates of detective quantum efficiency that are useful in rank-ordering of detector array functionality settings in conformance with identified characteristics of the test subject and goals associated with an imaging task relative to the test subject.

15. The system of claim 9, wherein the illumination source comprises an X-ray illumination source, and wherein the software operative on the processor is further configured to generate a message to an operator of the system prior to initiation of exposure of the test subject to X-rays.

16. The system of claim 8, further comprising:
the software operative on the processor for
estimating detective quantum efficiency for several of the multiple functionality settings for the detector array;
distinguishing among the several based on dose and image quality goals to provide one or more candidate functionality settings; and
selecting of one of the candidate functionality settings, wherein the controllable driver is configured to assist in determining a dose of X-radiation consistent with binning that reduces X-ray dose exposure of the test subject relative to the several.

17. A system for variable binning of detector data in an X-ray system, comprising:
a processor coupled to an X-ray detector;
a storage device coupled to the processor and having software operative on the processor for:
accepting input data indicative of image quality goals and information descriptive of a test subject to be characterized using the X-ray system; and
determining when the X-ray system is capable of achieving the image quality goals via combining the signals from an extended group of detector elements, wherein the capability is a reduction of one or more dose, spatial frequency response, detective quantum efficiency and other user defined variables;
performing binning analyses when the X-ray system is capable of achieving the image quality goals via combining the signals; and
setting the X-ray detector control circuitry and exposure parameters in accordance to the determination and binning analyses.

18. The system of claim 17, wherein the software is further operative on the processor for accepting revised computer-readable information descriptive of revised capabilities.

19. The system of claim 17, wherein the software is further configured to cause the processor to perform acts of:
accessing stored data descriptive of calculated estimates of detective quantum efficiency useful in rank-ordering of detector array functionality settings in conformance with identified characteristics of the test subject and goals associated with an imaging task relative to the test subject; and
selecting one or more of multiple X-ray exposure strategies.

20. The system of claim 17, wherein the software is further configured to cause the processor to perform acts of:
estimating detective quantum efficiency for multiple detector array functionality settings;
distinguishing among several detector array functionality settings based on dose and image quality goals to provide one or more candidate functionality settings; and
selecting one of the candidate functionality settings.

* * * * *